United States Patent
McGowan

(10) Patent No.: US 10,835,182 B2
(45) Date of Patent: Nov. 17, 2020

(54) MEDICAL DEVICE SYSTEMS INCLUDING AN OPTICAL FIBER WITH A TAPERED CORE

(71) Applicant: Boston Scientific Scimed, Inc., Maple Grove, MN (US)

(72) Inventor: Roger W. McGowan, Ostego, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 609 days.

(21) Appl. No.: 14/459,131

(22) Filed: Aug. 13, 2014

(65) Prior Publication Data

US 2015/0051499 A1  Feb. 19, 2015

Related U.S. Application Data

(60) Provisional application No. 61/865,713, filed on Aug. 14, 2013.

(51) Int. Cl.
*A61B 5/00* (2006.01)
*A61B 5/0215* (2006.01)

(52) U.S. Cl.
CPC .......... *A61B 5/6851* (2013.01); *A61B 5/0084* (2013.01); *A61B 5/02154* (2013.01)

(58) Field of Classification Search
CPC . A61B 5/6851; A61B 5/0084; A61B 5/02154; A61B 5/0215; A61B 2018/2244; A61B 2018/2277; A61B 2562/0247; A61M 2025/0002; A61M 25/09; G02B 6/262
See application file for complete search history.

(56) References Cited

U.S. PATENT DOCUMENTS

| | | |
|---|---|---|
| 3,963,323 A | 6/1976 | Arnold |
| 4,771,782 A | 9/1988 | Millar |
| 4,953,553 A | 9/1990 | Tremulis |
| 5,106,455 A | 4/1992 | Jacobsen et al. |
| 5,178,159 A | 1/1993 | Christian |
| 5,238,004 A | 8/1993 | Sahatjian et al. |
| 5,313,957 A | 5/1994 | Little |
| 5,421,195 A | 6/1995 | Wlodarczyk |
| 5,422,969 A | 6/1995 | Eno |
| 5,427,114 A | 6/1995 | Colliver et al. |
| 5,438,873 A * | 8/1995 | Wlodarczyk ...... A61B 5/02154 73/705 |
| 5,573,520 A | 11/1996 | Schwartz et al. |
| 5,633,963 A | 5/1997 | Rickenbach et al. |

(Continued)

FOREIGN PATENT DOCUMENTS

| | | | |
|---|---|---|---|
| DE | 202014100938 U1 | 3/2014 | |
| EP | 0235992 A1 | 9/1987 | |

(Continued)

*Primary Examiner* — Boniface N Nganga
(74) *Attorney, Agent, or Firm* — Seager, Tufte & Wickhem, LLP

(57) ABSTRACT

A medical device system may include a guidewire including a distal pressure sensor and a proximal end. A connector cable may be coupled to the proximal end of the guidewire and may have a proximal end. A signal conditioning unit may be coupled to the proximal end of the connector cable. One or more of the guidewire, the connector cable, and the signal conditioning unit may include an optical fiber having a core with a tapered outer diameter.

19 Claims, 7 Drawing Sheets

(56) References Cited

U.S. PATENT DOCUMENTS

| | | | |
|---|---|---|---|
| 5,755,668 A | 5/1998 | Itoigawa et al. | |
| 5,772,609 A | 6/1998 | Nguyen et al. | |
| 5,797,856 A | 8/1998 | Frisbie et al. | |
| 5,872,879 A | 2/1999 | Hamm | |
| 5,902,248 A | 5/1999 | Millar et al. | |
| 5,938,624 A | 8/1999 | Akerfeldt et al. | |
| 5,949,929 A | 9/1999 | Hamm | |
| 6,112,598 A | 9/2000 | Tenerz et al. | |
| 6,120,457 A | 9/2000 | Coombes et al. | |
| 6,139,510 A | 10/2000 | Palmero | |
| 6,162,182 A | 12/2000 | Cole | |
| 6,167,763 B1 | 1/2001 | Tenerz et al. | |
| 6,196,980 B1 | 3/2001 | Akerfeldt et al. | |
| 6,248,083 B1 | 6/2001 | Smith et al. | |
| 6,265,792 B1 | 7/2001 | Granchukoff | |
| 6,394,986 B1 | 5/2002 | Millar | |
| 6,398,738 B1 | 6/2002 | Millar | |
| 6,409,677 B1 | 6/2002 | Tulkki | |
| 6,428,336 B1 | 8/2002 | Akerfeldt | |
| 6,508,803 B1 | 1/2003 | Horikawa et al. | |
| 6,565,514 B2 | 5/2003 | Svanerudh et al. | |
| 6,579,246 B2 | 6/2003 | Jacobsen et al. | |
| 6,585,660 B2 | 7/2003 | Dorando et al. | |
| 6,615,067 B2 | 9/2003 | Hoek et al. | |
| 6,663,570 B2 | 12/2003 | Mott et al. | |
| 6,766,720 B1 | 7/2004 | Jacobsen et al. | |
| 6,767,327 B1 | 7/2004 | Corl et al. | |
| 6,776,720 B2 | 8/2004 | Bartlett | |
| 6,908,442 B2 | 6/2005 | Von Malmborg et al. | |
| 6,918,882 B2 | 6/2005 | Skujins et al. | |
| 6,918,873 B2 | 7/2005 | Millar et al. | |
| 6,974,422 B1 | 12/2005 | Millar | |
| 6,976,965 B2 | 12/2005 | Corl et al. | |
| 6,993,974 B2 | 2/2006 | Tenerz et al. | |
| 6,994,695 B1 | 2/2006 | Millar | |
| 7,071,197 B2 | 7/2006 | Leonardi et al. | |
| 7,134,994 B2 | 11/2006 | Alpert et al. | |
| 7,162,926 B1 | 1/2007 | Guziak et al. | |
| 7,187,453 B2 | 3/2007 | Belleville | |
| 7,259,862 B2 | 8/2007 | Duplain et al. | |
| 7,265,847 B2 | 9/2007 | Duplain et al. | |
| 7,274,956 B2 | 9/2007 | Mott et al. | |
| 7,331,236 B2 | 2/2008 | Smith et al. | |
| 7,532,920 B1* | 5/2009 | Ainsworth | A61B 5/02007 600/341 |
| 7,618,379 B2 | 11/2009 | Reynolds et al. | |
| 7,684,657 B2 | 3/2010 | Donlagic et al. | |
| 7,689,071 B2 | 3/2010 | Belleville et al. | |
| 7,715,903 B2 | 5/2010 | Hartley et al. | |
| 7,724,148 B2 | 5/2010 | Samuelsson et al. | |
| 7,731,664 B1 | 6/2010 | Millar | |
| 7,759,633 B2 | 7/2010 | Duplain et al. | |
| 7,783,338 B2 | 8/2010 | Ainsworth et al. | |
| 7,878,984 B2 | 2/2011 | Davis et al. | |
| 7,930,014 B2 | 4/2011 | Huenneckens et al. | |
| 7,946,997 B2 | 5/2011 | Hübinette | |
| 8,025,623 B1 | 9/2011 | Millar | |
| 8,029,447 B2 | 10/2011 | Kanz et al. | |
| 8,174,395 B2 | 5/2012 | Samuelsson et al. | |
| 8,216,151 B2 | 7/2012 | Smith | |
| 8,298,156 B2 | 10/2012 | Manstrom et al. | |
| 8,317,715 B2 | 11/2012 | Belleville et al. | |
| 8,343,076 B2 | 1/2013 | Sela et al. | |
| 8,410,940 B2 | 4/2013 | Samuelsson et al. | |
| 8,461,997 B2 | 6/2013 | Samuelsson et al. | |
| 8,485,985 B2 | 7/2013 | Manstrom et al. | |
| 8,491,484 B2* | 7/2013 | Lewis | A61B 5/6851 600/459 |
| 8,555,712 B2 | 10/2013 | Narvaez et al. | |
| 8,556,820 B2 | 10/2013 | Alpert et al. | |
| 8,562,537 B2 | 10/2013 | Alpert et al. | |
| 8,583,218 B2 | 11/2013 | Eberle | |
| 8,636,659 B2 | 1/2014 | Alpert et al. | |
| 8,641,633 B2 | 2/2014 | Smith | |
| 8,641,639 B2 | 2/2014 | Manstrom et al. | |
| 8,676,299 B2 | 3/2014 | Schmitt et al. | |
| 8,698,638 B2 | 4/2014 | Samuelsson et al. | |
| 8,752,435 B2 | 6/2014 | Belleville et al. | |
| 8,936,401 B2 | 1/2015 | Belleville et al. | |
| 8,998,823 B2 | 4/2015 | Manstrom et al. | |
| 9,052,466 B2 | 6/2015 | Belleville et al. | |
| 2003/0069522 A1 | 4/2003 | Jacobsen et al. | |
| 2004/0073141 A1 | 4/2004 | Hartley et al. | |
| 2004/0181174 A2 | 9/2004 | Davis et al. | |
| 2005/0000294 A1 | 1/2005 | Tenerz et al. | |
| 2006/0122537 A1 | 6/2006 | Reynolds et al. | |
| 2007/0010726 A1* | 1/2007 | Loeb | A61B 5/14532 600/317 |
| 2008/0119758 A1 | 5/2008 | Samuelsson et al. | |
| 2009/0082678 A1 | 3/2009 | Smith | |
| 2009/0192412 A1 | 7/2009 | Sela et al. | |
| 2010/0145308 A1 | 6/2010 | Layman et al. | |
| 2010/0241008 A1 | 9/2010 | Belleville et al. | |
| 2011/0071407 A1 | 3/2011 | Hubinette et al. | |
| 2011/0178413 A1 | 7/2011 | Schmitt et al. | |
| 2011/0186294 A1 | 8/2011 | Narvaez et al. | |
| 2011/0319773 A1 | 12/2011 | Kanz et al. | |
| 2012/0227505 A1 | 9/2012 | Belleville et al. | |
| 2012/0265102 A1 | 10/2012 | Leo et al. | |
| 2013/0051731 A1 | 2/2013 | Belleville et al. | |
| 2013/0218032 A1 | 8/2013 | Belleville | |
| 2013/0296718 A1 | 11/2013 | Ranganathan et al. | |
| 2013/0317372 A1 | 11/2013 | Eberle et al. | |
| 2014/0005558 A1 | 1/2014 | Gregorich | |
| 2014/0058275 A1 | 2/2014 | Gregorich et al. | |
| 2014/0081244 A1 | 3/2014 | Voeller et al. | |
| 2014/0107624 A1 | 4/2014 | Belleville | |
| 2014/0121475 A1 | 5/2014 | Alpert et al. | |
| 2014/0241669 A1 | 8/2014 | Belleville et al. | |
| 2014/0248021 A1 | 9/2014 | Belleville et al. | |
| 2014/0309533 A1* | 10/2014 | Yamashita | A61M 25/0009 600/463 |
| 2015/0141842 A1* | 5/2015 | Spanier | A61B 5/02154 600/478 |

FOREIGN PATENT DOCUMENTS

| | | | |
|---|---|---|---|
| EP | 0738495 A1 | 10/1996 | |
| EP | 0879615 A1 | 11/1998 | |
| EP | 0879617 A1 | 11/1998 | |
| EP | 1479407 A1 | 11/2004 | |
| JP | 10501339 A1 | 2/1998 | |
| JP | 2011228541 A | * 11/2011 | |
| WO | 9313707 A1 | 7/1993 | |
| WO | 9533983 A1 | 12/1995 | |
| WO | 9945352 A1 | 9/1999 | |
| WO | 2008034010 A2 | 3/2008 | |
| WO | 2011027282 A1 | 3/2011 | |
| WO | 2011090744 A2 | 7/2011 | |
| WO | 2011123689 A1 | 10/2011 | |
| WO | 2012000798 A1 | 1/2012 | |
| WO | 2012090210 A1 | 7/2012 | |
| WO | 2013033489 A1 | 3/2013 | |
| WO | 2014025255 A1 | 2/2014 | |

* cited by examiner

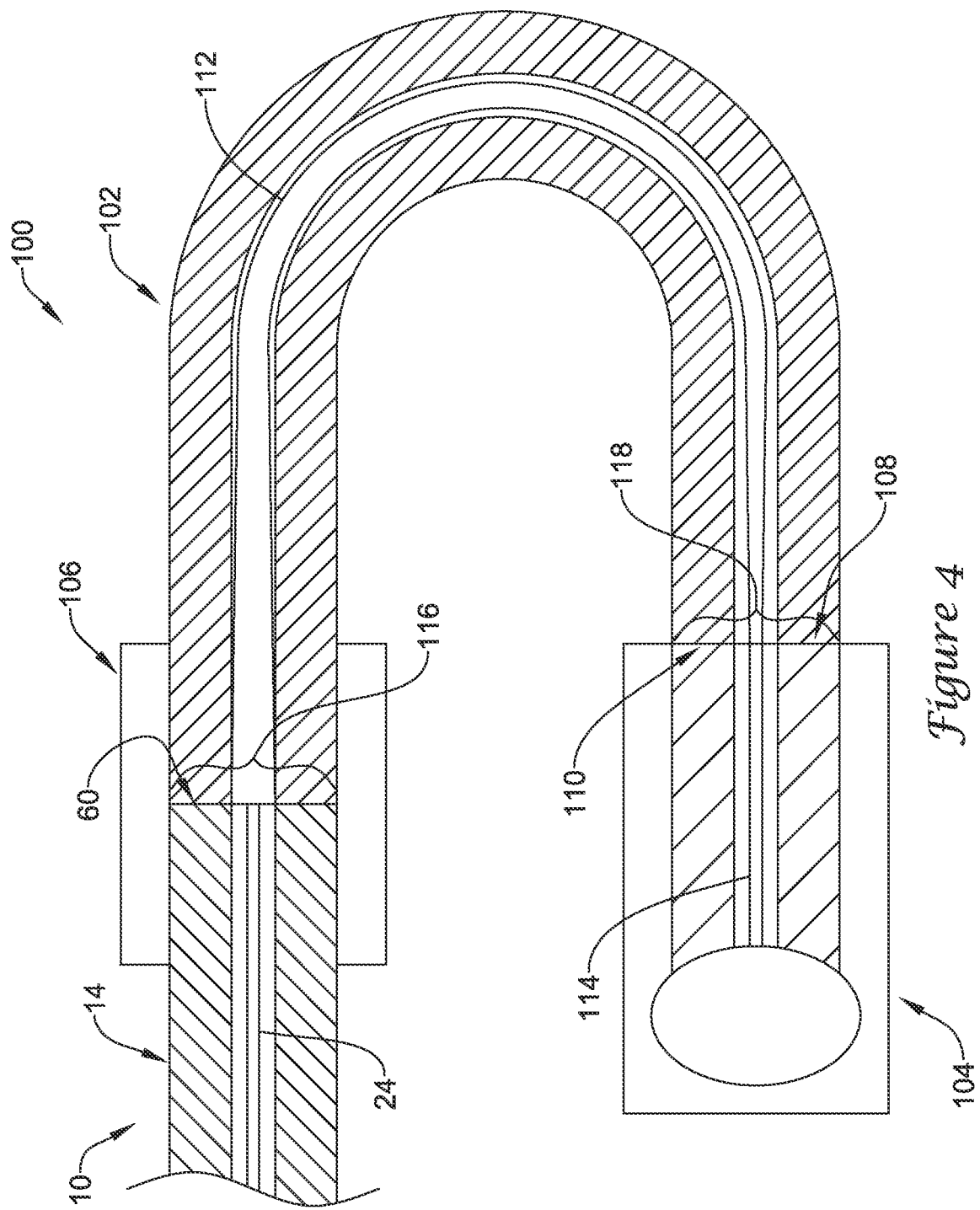

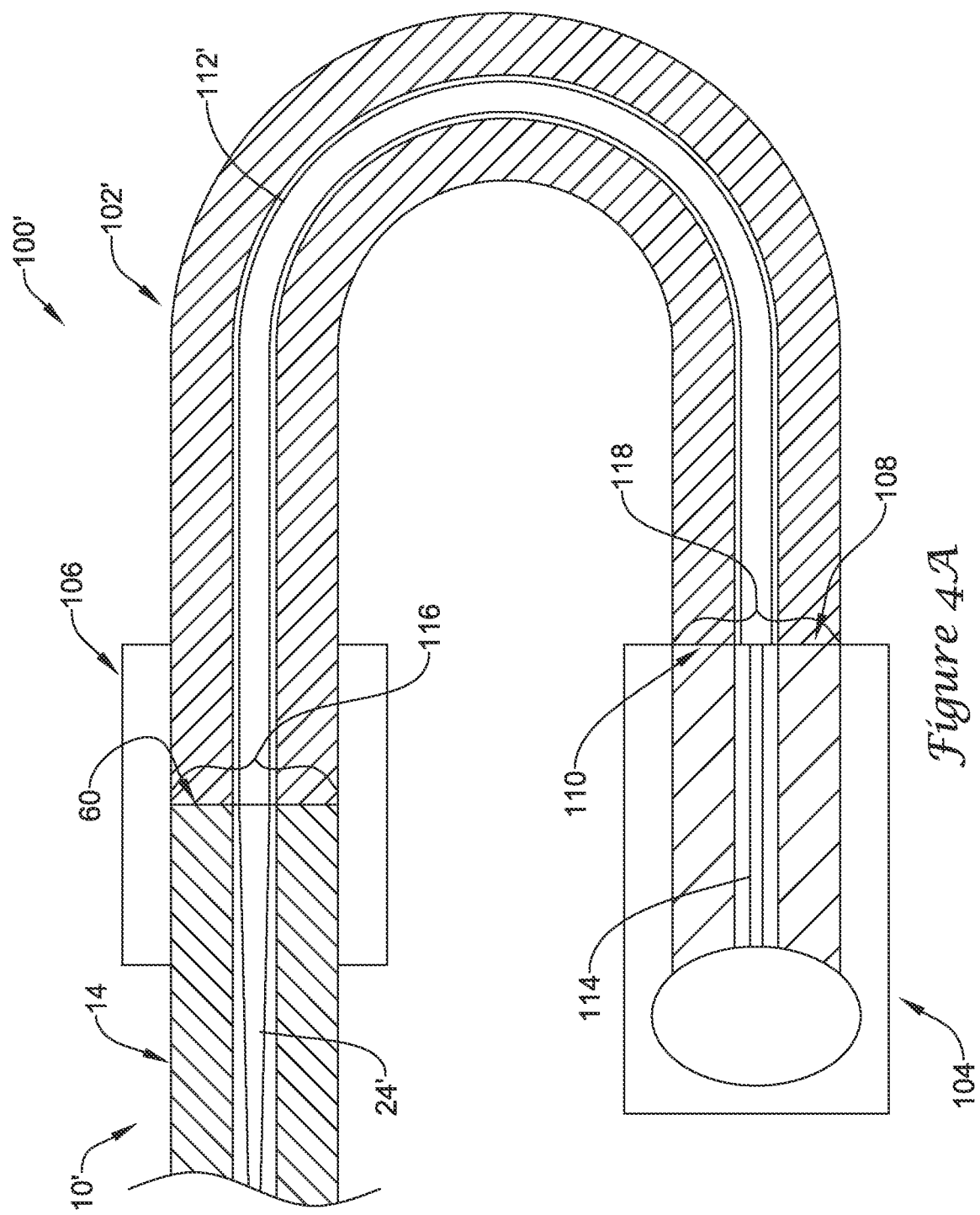

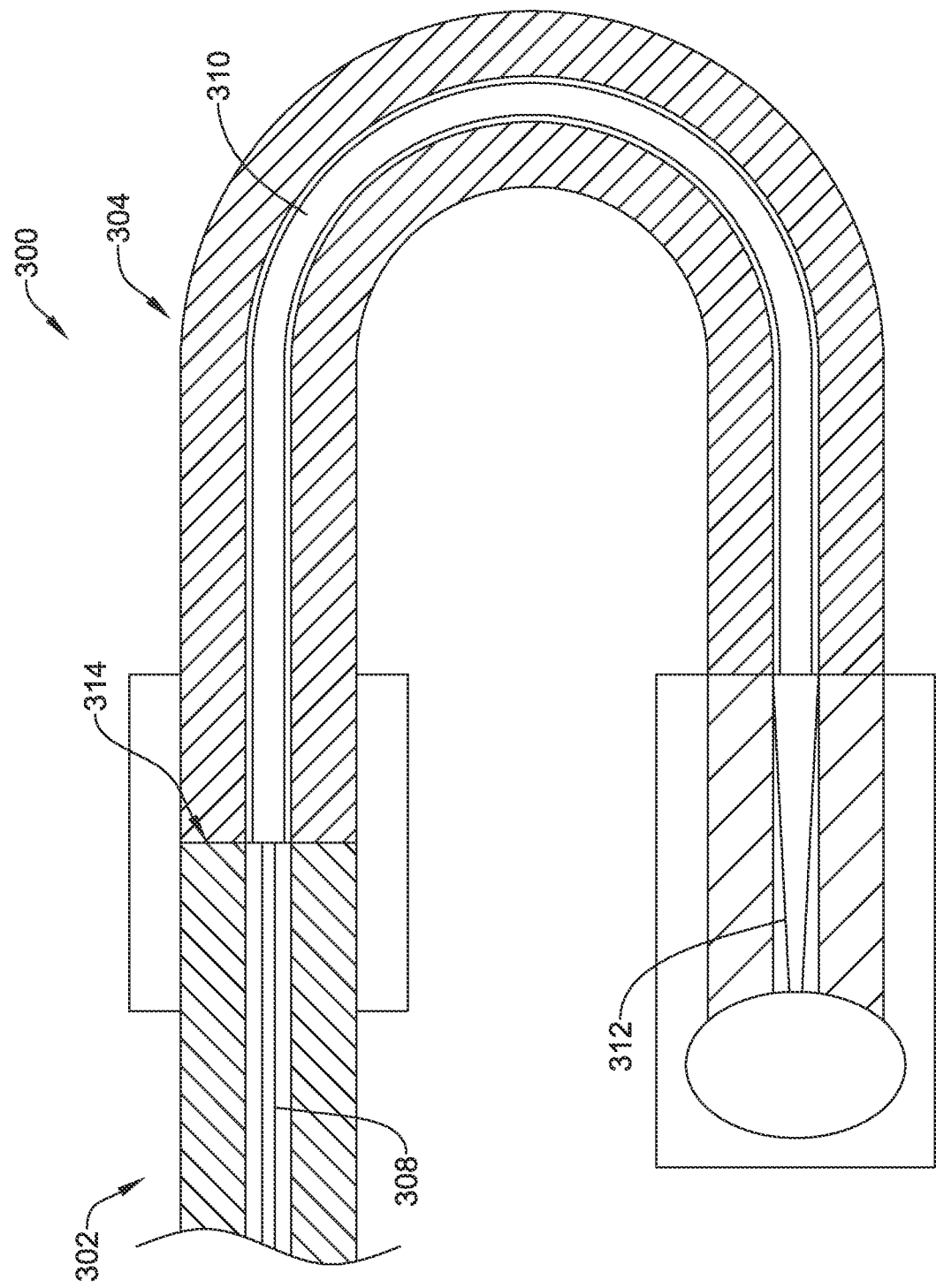

MEDICAL DEVICE SYSTEMS INCLUDING AN OPTICAL FIBER WITH A TAPERED CORE

CROSS-REFERENCE TO RELATED APPLICATIONS

This application claims priority under 35 U.S.C. § 119 to U.S. Provisional Application Ser. No. 61/865,713, filed Aug. 14, 2013, the entirety of which is incorporated herein by reference.

TECHNICAL FIELD

The present disclosure pertains to medical devices/systems, and methods for manufacturing medical devices. More particularly, the present disclosure pertains to medical device systems that include optical fibers having a tapered core.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices and medical device systems. An example medical device system may include a guidewire. The guidewire may include a distal pressure sensor and a proximal end. A connector cable may be coupled to the proximal end of the guidewire. The connector cable may have a proximal end. A signal conditioning unit may be coupled to the proximal end of the connector cable. One or more of the guidewire, the connector cable, and the signal conditioning unit may include an optical fiber having a core with a tapered outer diameter.

Another example medical device system may include a guidewire. The guidewire may include an optical pressure sensor and a first optical fiber extending therefrom. A connector cable may be capable of being coupled to a proximal end of the guidewire. The connector cable may include a second optical fiber that is capable of being coupled to the first optical fiber. A signal conditioning unit may be capable of being coupled to the connector cable. The signal conditioning unit may include a third optical fiber that may be capable of being coupled to the second optical fiber. At least one of the second optical fiber and the third optical fiber may include a core having at least a region with a tapered outer diameter.

Another example medical device system for determining fractional flow reserve may include a guidewire. The guidewire may include an optical pressure sensor and a first optical fiber extending therefrom. A connector cable may be capable of being coupled to a proximal end of the guidewire. The connector cable may include a second optical fiber that may be capable of being coupled to the first optical fiber. The second optical fiber may include a core having at least a region with a tapered outer diameter. A signal conditioning unit may be capable of being coupled to the connector cable. The signal conditioning unit may include a third optical fiber that is capable of being coupled to the second optical fiber.

Another example medical device system for determining fractional flow reserve may include a guidewire. The guidewire may include an optical pressure sensor and a first optical fiber may extend therefrom. A connector cable may be capable of being coupled to a proximal end of the guidewire. The connector cable may include a second optical fiber that may be capable of being coupled to the first optical fiber. A signal conditioning unit may be capable of being coupled to the connector cable. The signal conditioning unit may include a third optical fiber that may be capable of being coupled to the second optical fiber. The third optical fiber may include a core having at least a region with a tapered outer diameter.

The above summary of some embodiments of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 4 is a partial cross-sectional schematic illustration depicting an exemplary medical device system;

FIG. 4A is a partial cross-sectional schematic illustration depicting another exemplary medical device system; FIG. 6 is a partial cross-sectional schematic illustration depicting another exemplary medical device system.

Figure 1:
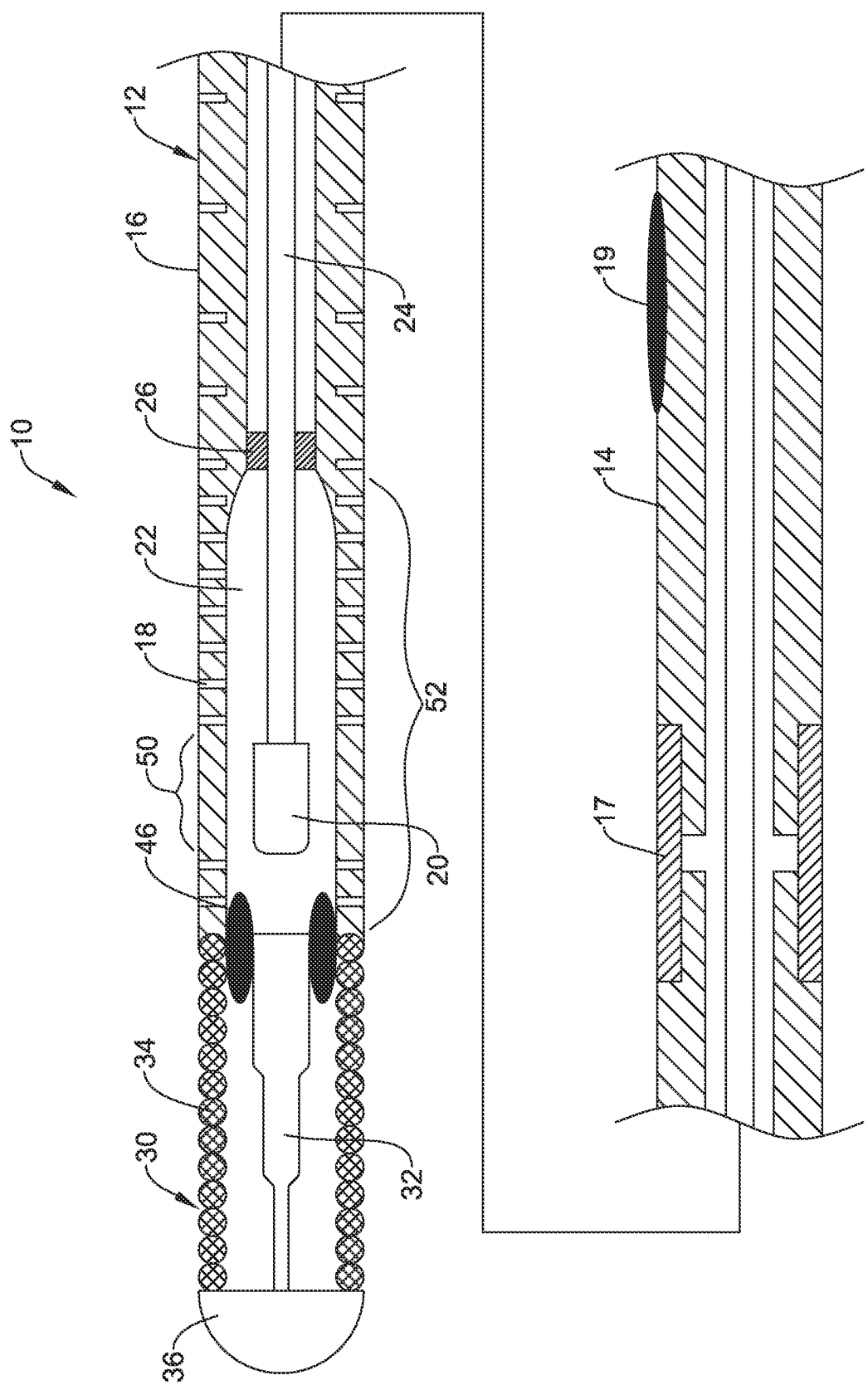
FIG. 1 is a partial cross-sectional side view of an example guidewire.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as the pressure after a stenosis relative to the pressure before the stenosis. The FFR measurement may be used to determine whether or not a medical procedure such as angioplasty, stent delivery, or the like is appropriate.

FIG. 1 shows a guidewire that may be used in the present medical device system. The guidewire 10 may include a tubular member or shaft 12 having a proximal portion 14 and a distal portion 16. The distal portion 16 may include a sensor region 52 and a tip region 30. The sensor region 52 may include an optical pressure sensor 20 attached at a distal end of an optical fiber 24 disposed within a lumen of the shaft 12. The term 'optical pressure sensor 20' may be referred as 'sensor 20' herein throughout the detailed description. The sensor 20 may be employed to measure blood pressure within blood vessel. In some embodiments, the pressure measurements made by the sensor 20 may be utilized to calculate FFR. In at least some embodiments, the sensor 20 is a Fabry-Perot type pressure sensor.

The optical fiber 24 may have a substantially constant outer diameter along its length. A distal portion of the optical fiber 24 may be attached to inner wall of the shaft 12 via a bond 26. Such attachment may be located proximal to an enlarged region 22. The enlarged region 22 may be defined as a region having an increased inner diameter than that of remaining portion of the shaft 12. Such region having an enlarged diameter may be employed to house the sensor 20.

The tip region 30 may include a coil 34, and a tip member 36. The tip region 30 may be disposed at the distal end of the shaft 12. One end of the coil 34 may be positioned adjacent the tip member 36 and another end of the coil 34 may be positioned adjacent the sensor region 52. The coil 34 may be positioned proximally adjacent to the tip member 36, and may provide flexibility to the tip member 36. The coil 34 may be disposed circumferentially around a shaping member 32 that is disposed at a distal end of the sensor region 52, and within the tip region 30. The tip member 36 may be disposed at a distal end of the shaping member 32. The shaping member 32 may be made, for example, from a deformable material so that it may be able to deform and hold shape of the tip member 36 whenever the tip region 30 bends while traversing through blood vessels. The shaping member 32 may be bonded to the distal end of the shaft 12, and a proximal end of the coil 34 at a bond 46. These are just examples. Other structures, features, and arrangements are contemplated.

The guidewire 10 may include a number of other structural features. For example, an outer surface of the shaft 12 may include a number of slots 18. The slots 18 may be arranged circumferentially and along a longitudinal axis of the shaft 12 such that the adjacent slots 18 may be spaced apart. As shown in FIG. 1, the density of the slots 18 increases distally allowing for more flexibility toward the distal end of the shaft 12. A distal portion 16 of the shaft 12 may include a solid region 50 which may not have any slots 18. The region 50 may be provided to avoid direct contact of the sensor 20 with blood, thereby preventing deflection of the side surfaces of the sensor 20, which could alter the blood pressure reading.

In some cases, the proximal portion 14 and the distal portion 16 of the guidewire 10 made from different materials may be connected via a connector 17. However, the proximal portion 14 and the distal portion 16 may also be unitary structure. The shaft 12 may be coated wholly or partially with a hydrophilic coating 19 to reduce friction of the outer surface of the guidewire 10, thereby making the navigation of the guidewire 10 through the blood vessel smooth. The above descriptions of the guidewire 10 are just examples. Other structures are contemplated for the guidewire 10.

Figure 2:
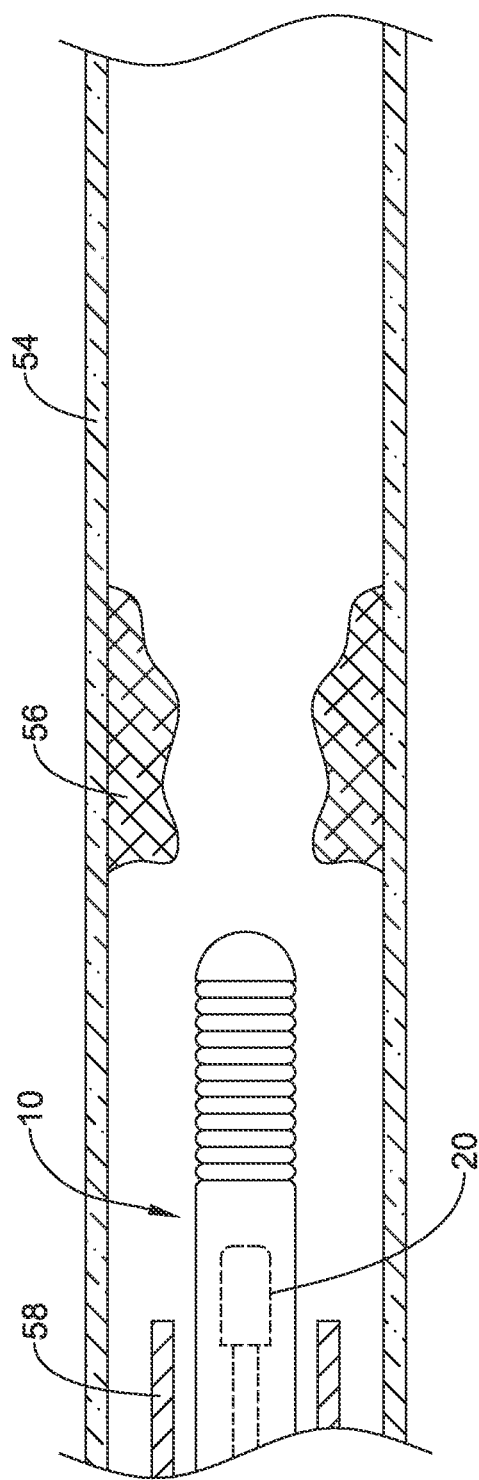
FIGS. 2 and 3 are schematic illustrations depicting measurement of FFR (Fractional Flow Reserve) using an exemplary guidewire.
Figure 3:
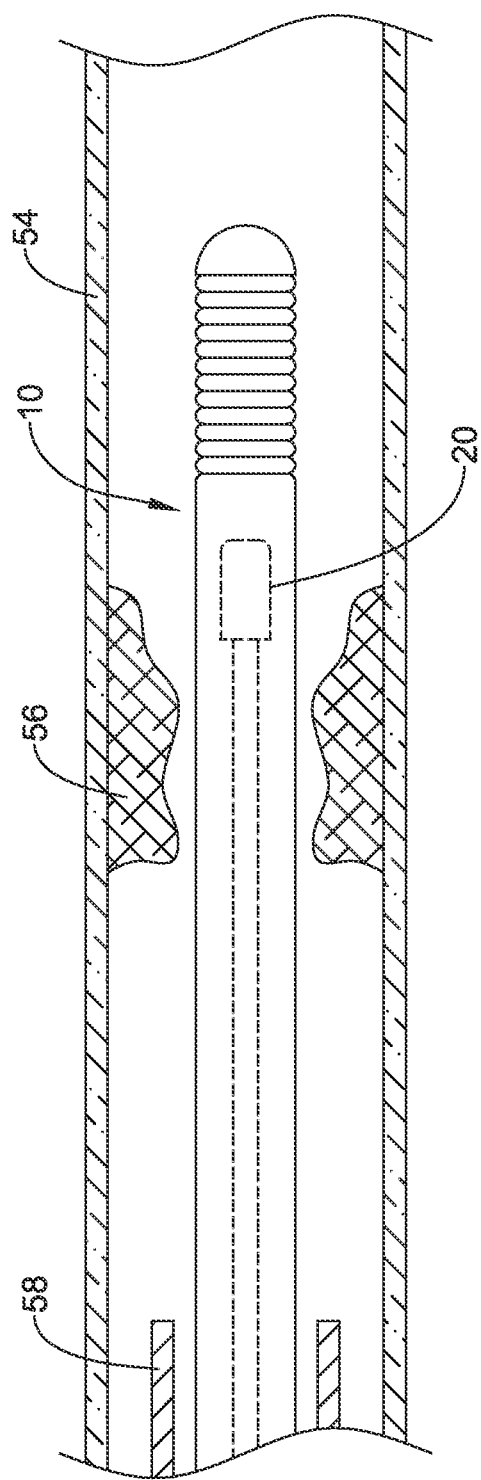

As suggested above, the guidewire 10 may be used to measure blood pressure of a portion upstream and downstream the stenosis to determine FFR, methods of which are explained in conjunction with FIGS. 2 and 3. As shown in FIG. 2, the guidewire 10 may traverse through a blood vessel 54 to reach a target site (e.g., a lesion 56). The guidewire 10 may measure a first reading of the blood pressure before the lesion 56. Alternatively, another medical device may be utilized to measure blood pressure, for example, the aortic blood pressure. Thereafter, the guidewire 10 may be advanced distally past the lesion 56 to take a second reading of the blood pressure after the lesion 56 as shown in FIG. 3. The ratio of the two blood pressure readings (e.g., the pressure downstream of the lesion and the pressure upstream of the lesion or the aortic pressure) may determine FFR, thereby helping to assess whether or not to perform angioplasty or stenting. A guide catheter 58 may be provided for delivering or advancing treatment devices such as stent, balloon, etc. at the desired treatment location.

As also suggested above, the guidewire 10 may include an optical pressure sensor 20 and an optical fiber 24. While using optical cables and/or optical fibers, the alignment of the optical fibers may be desirable. Even a slight misalignment of the optical fibers may lead to signal losses, which could skew, for example, communication between the fibers and may impact pressure measurements. For example, a standard optical fiber may have a 62.5 μm core. For the purposes of this disclosure, the core may be understood as the region of the optical fiber 24 (and/or other optical fibers disclosed herein) that guides the light. In optical fiber connections, an offset from a centerline of the connection can cause a loss of signal and disrupt the medical procedure. For example, an offset of 15-20 μm or less may lead to signal loss. Accordingly, it may be desirable to design optical fibers that allow for easy and reproducible alignment of the fibers for robust connections. The present medical device system incorporates one or more structural features that may help to improve the communication between optical fibers.

FIG. 4 is a cross-sectional schematic illustration depicting an exemplary medical device system 100. The medical device system 100 may include the guidewire 10 (e.g., as shown in FIGS. 1-3), a connector cable 102, and a signal conditioning unit 104. The connector cable 102 may include a distal connector 106 and a proximal connector 118. The connector cable 102 may be attached to a proximal end 60 of the guidewire 10 via the distal connector 106. The connector cable 102 may be connected to the signal conditioning unit 104 and the proximal connector 118. The connector cable 102 may be provided as a mediator to connect the guidewire 10 with the signal conditioning unit 104. The signal conditioning unit 104 may be connected to a suitable display unit (not shown).

The connector cable 102 and the signal conditioning unit 104 may include a second optical fiber 112 and the third optical fiber 114 respectively. The optical fiber 24 may have an outer diameter and/or a core outer diameter. For example, outer diameter of the core of optical fiber 24 may be about 40-80 µm, or about 50-70 µm, or about 62.5 µm. These are just examples. Other sizes are contemplated. The second optical fiber 112 may have a core with an outer diameter that tapers between the proximal end and the distal end thereof as shown in FIG. 4. For example, one end of the second optical fiber 112 may have a relatively larger core outer diameter and the other end may have a core outer diameter that is reduced relative to the larger core outer diameter. In at least some embodiments, the distal end of the second optical fiber 112 has a core outer diameter that is larger than the core outer diameter of the optical fiber 24. For example, the distal end of the second optical fiber 112 may have a core outer diameter greater than 62.5 µm, or about 75-150 µm, or about 80-120 µm, or about 100 µm. The proximal end of the second optical fiber 112 may have a core outer diameter that is reduced relative to the core outer diameter at the distal end. In some embodiments, the proximal end of the second optical fiber 112 may have a core outer diameter that approximates or otherwise is substantially the same as the core outer diameter of the optical fiber 24.

As indicated above, if the optical fiber 24 and the second optical fiber 112 have essentially the same core diameter, a slight misalignment between the two optical fibers could result in a signal loss. However, if the second optical fiber 112 has a larger core outer diameter compared to that of the optical fiber 24, then the second optical fiber 112 would essentially cover the proximal end of the optical fiber 24 fully. As a result, the entire signal from the optical fiber 24 may be captured at the second optical fiber 112 even if there is a slight misalignment of the fibers 24, 112. More particularly, signal passing distally from the second optical fiber 112 to the optical fiber 24 (e.g., the outbound signal) may have an anticipated or designed loss. However, signal passing distally from the optical fiber 24 to the second optical fiber 112 (e.g., the return signal) may have minimal or essentially no signal loss.

The dimensions of the tapered second optical fiber 112 in the connector cable 102 may be defined so as to allow the connection to be within allowable tolerances. Also, the tapered optical fibers may be designed to have a numerical aperture such that the optical fiber may be capable of receiving substantially all of a signal passing through the optical fiber. Hence, the tapered optical fiber allows for good communication even when there is a bit of offset.

At the connector 106, the optical fiber 24 and the second optical fiber 112 may come together at an intersection surface 116. At the intersection surface 116, signal may be communicated between the optical fiber 24 and the second optical fiber 112. The optical fibers 24, 112, and 114 may be multimode. Also, a protective covering such as a sheath or a sleeve may be disposed over the optical fibers 24, 112, and 114.

As shown in FIG. 4, the optical fiber 24 may have a core diameter lesser than that of a distal end of the tapered second optical fiber 112, and a proximal end of the tapered second optical fiber 112 may have same core diameter as that of the third optical fiber 114. The optical fiber 24 and the third optical fiber 114 may have the same core diameter uniformly throughout their length while the second optical fiber 112 may be a tapered optical fiber. These are just examples. Other arrangements are contemplated. For example, FIG. 4A illustrates a medical device system 100' where the guidewire 10' may include an optical fiber 24' with a tapered core. In this example, the core of the optical fiber 24' tapers in the distal direction (e.g., gets smaller distally). The connector cable 102' may have an optical fiber 112' having a core with a diameter that may be the same as or larger than the diameter of the core of the optical fiber 24'.

Figure 5:
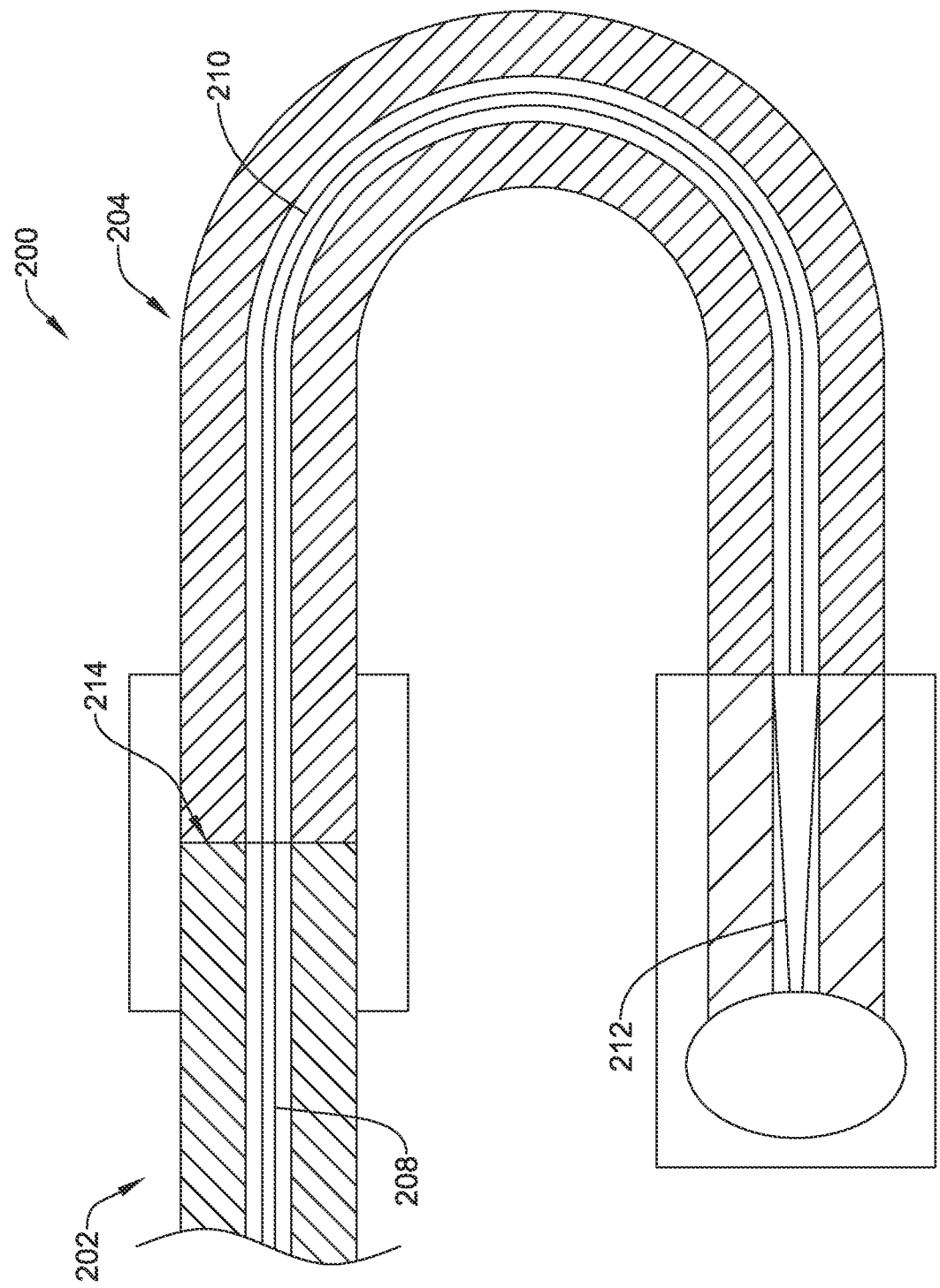
FIG. 5 is a partial cross-sectional schematic illustration depicting another exemplary medical device system.

FIG. 5 is a cross-sectional schematic illustration depicting another exemplary medical device system 200. The medical device system 200 may include the guidewire 202, the connector cable 204, and the signal conditioning unit 206. Each of the guidewire 202, the connector cable 204, and the signal conditioning unit 206 may have optical fibers 208, 210, 212 respectively. The guidewire 202 may be connected to the connector cable 204 via a connector 214. Although the structure of the medical device system 200 is similar to that of the medical device system 100, the first optical fiber 208 may have same core diameter as that of the second optical fiber 210. Each of the first optical fiber 208 and the second optical fiber 210 may have a substantially constant core outer diameter along their respective lengths. However, the third optical fiber 212 may have a core that is tapered as shown in FIG. 5.

In some embodiments, the third optical fiber 212 may have a first end where the core outer diameter is relatively larger and a second end where the core outer diameter is reduced relative to the larger core outer diameter. For example, the first end of the third optical fiber 212 may have a core diameter that is greater than 62.5 µm, or about 75-150 µm, or about 80-120 µm, or about 100 µm. The other end of the third optical fiber 212 may have a core diameter that that approximates or otherwise is substantially the same as the core outer diameter of the second optical fiber 210. The third optical fiber 212 may be capable of receiving substantially all of a signal passing through the second optical fiber 210. In at least some other embodiments, one or both of the second optical fiber 210 and the third optical fiber 212 may have tapered core diameter while the first optical fiber 208 may have uniform diameter throughout along its length.

While not explicitly shown, in some embodiments, the second optical fiber 210 may have a core diameter that is enlarged relative to that of the optical fiber 208. For example, the optical fiber 208 may have a core with an outer diameter of about 40-80 µm, or about 50-70 µm, or about 62.5 µm. Second optical fiber 210 may have a core outer diameter greater than 62.5 µm, or about 75-150 µm, or about 80-120 µm, or about 100 µm. In some embodiments, the outer diameter of the core of the second optical fiber 210 may be substantially constant along its length. The distal end of the third optical fiber 212 may be tapered. For example, the first end of the third optical fiber 212 may have a core diameter that is greater than 62.5 µm, or about 75-150 µm, or about 80-120 µm, or about 100 µm while the other end of the third optical fiber 212 may have a core diameter that that approximates or otherwise is substantially the same as the core outer diameter of the optical fiber 208.

FIG. 6 is a cross-sectional schematic illustration depicting another exemplary medical device system 300. The medical device system 300 may include the guidewire 302, the connector cable 304, and the signal conditioning unit 306. Each of the guidewire 302, the connector cable 304, and the signal conditioning unit 306 may have optical fibers 308, 310, 312 respectively. The guidewire 302 may be connected to the connector cable 304 via a connector 314. The second optical fiber 310 may have a core with a diameter that is larger than the core of the first optical fiber 308. The third optical fiber 312 may have a core that is tapered. The larger end (e.g., the more distal end) of the third optical fiber 312 may have a core diameter that is the same size or larger than the core diameter of the second optical fiber 310.

The materials that can be used for the various components of the systems presently disclosed may include those commonly associated with medical devices. For simplicity purposes, the following discussion makes reference to guidewire 10. However, this is not intended to limit the devices and methods described herein, as the discussion may be applied to other similar devices and/or components of devices and systems disclosed herein.

The guidewire 10 and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "super elastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota).

In at least some embodiments, portions or all of the guidewire 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the guidewire 10 in determining its location. Some examples of radiopaque materials can include, but are not limited to, gold, platinum, palladium, tantalum, tungsten alloy, polymer material loaded with radiopaque filler, and the like. Additionally, other radiopaque marker bands and/or coils may also be incorporated into the design of the guidewire 10 to achieve the same result.

In some embodiments, a degree of Magnetic Resonance Imaging (MRI) compatibility is imparted into the guidewire 10. For example, guidewire 10 or portions thereof may be made of a material that does not substantially distort the image and create substantial artifacts (i.e., gaps in the image). Certain ferromagnetic materials, for example, may not be suitable because they may create artifacts in an MRI image. The guidewire 10 or portions thereof may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

As alluded to above, the shaft 12 may include one or more tubular members that may have slots 18 formed therein. Various embodiments of arrangements and configurations of slots 18 are contemplated. For example, in some embodiments, at least some, if not all of the slots 18 are disposed at the same or a similar angle with respect to the longitudinal axis of the shaft 12. As shown, the slots 18 can be disposed at an angle that is perpendicular, or substantially perpendicular, and/or can be characterized as being disposed in a plane that is normal to the longitudinal axis of the shaft 12. However, in other embodiments, the slots 18 can be disposed at an angle that is not perpendicular, and/or can be characterized as being disposed in a plane that is not normal to the longitudinal axis of the shaft 12. Additionally, a group of one or more the slots 18 may be disposed at different angles relative to another group of one or more the slots 18. The distribution and/or configuration of the slots 18 can also include, to the extent applicable, any of those disclosed in U.S. Pat. Publication No. US 2004/0181174, the entire disclosure of which is herein incorporated by reference.

The slots 18 may be provided to enhance the flexibility of the shaft 12 while still allowing for suitable torque transmission characteristics. The slots 18 may be formed such that one or more rings and/or tube segments interconnected by one or more segments and/or beams that are formed in the shaft 12, and such tube segments and beams may include portions of the shaft 12 that remain after the slots 18 are formed in the body of the shaft 12. Such an interconnected structure may act to maintain a relatively high degree of torsional stiffness, while maintaining a desired level of lateral flexibility. In some embodiments, some adjacent the slots 18 can be formed such that they include portions that overlap with each other about the circumference of the shaft 12. In other embodiments, some adjacent the slots 18 can be disposed such that they do not necessarily overlap with each other, but are disposed in a pattern that provides the desired degree of lateral flexibility.

Additionally, the slots 18 can be arranged along the length of, or about the circumference of, the shaft 12 to achieve desired properties. For example, adjacent the slots 18, or groups of the slots 18, can be arranged in a symmetrical pattern, such as being disposed essentially equally on opposite sides about the circumference of the shaft 12, or can be rotated by an angle relative to each other about the axis of the shaft 12. Additionally, adjacent the slots 18, or groups of the slots 18, may be equally spaced along the length of the shaft 12, or can be arranged in an increasing or decreasing density pattern, or can be arranged in a non-symmetric or irregular pattern. Other characteristics, such as slot 18 size, slot 18 shape, and/or slot 18 angle with respect to the longitudinal axis of the shaft 12, can also be varied along the length of the shaft 12 in order to vary the flexibility or other properties. In other embodiments, moreover, it is contemplated that the portions of the tubular member, such as a proximal section, or a distal section, or the entire shaft 12, may not include any such the slots 18.

As suggested herein, the slots 18 may be formed in groups of two, three, four, five, or more the slots 18, which may be located at substantially the same location along the axis of the shaft 12. Alternatively, a single slot 18 may be disposed at some or all of these locations. Within the groups of the slots 18, there may be included the slots 18 that are equal in size (i.e., span the same circumferential distance around the shaft 12). In some of these as well as other embodiments, at least some the slots 18 in a group are unequal in size (i.e., span a different circumferential distance around the shaft 12). Longitudinally adjacent groups of the slots 18 may have the same or different configurations. For example, some embodiments of the shaft 12 include the slots 18 that are equal in size in a first group and then unequally sized in an adjacent group. It can be appreciated that in groups that have two slots 18 that are equal in size and are symmetrically disposed around the tube circumference, the centroid of the pair of beams (i.e., the portion of the shaft 12 remaining after the slot 18 are formed therein) is coincident with the central axis of the shaft 12. Conversely, in groups that have two the slots 18 that are unequal in size and whose centroids are directly opposed on the tube circumference, the centroid of the pair of beams can be offset from the central axis of the shaft 12. Some embodiments of the shaft 12 include only slot 18 groups with centroids that are coincident with the central axis of the shaft 12, only slot 18 groups with centroids that are offset from the central axis of the shaft 12, or slot 18 groups with centroids that are coincident with the central axis of the shaft 12 in a first group and offset from the central axis of the shaft 12 in another group. The amount of offset may vary depending on the depth (or length) of the slots 18 and can include other suitable distances.

The slots 18 can be formed by methods such as micromachining, saw-cutting (e.g., using a diamond grit embedded semiconductor dicing blade), electron discharge machining, grinding, milling, casting, molding, chemically etching or treating, or other known methods, and the like. In some such embodiments, the structure of the shaft 12 is formed by cutting and/or removing portions of the tube to form the slots 18. Some example embodiments of appropriate micromachining methods and other cutting methods, and structures for tubular members including slots 18 and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 10 may include forming the slots 18 in the shaft 12 using these or other manufacturing steps.

In at least some embodiments, the slots 18 may be formed in tubular member using a laser cutting process. The laser cutting process may include a suitable laser and/or laser cutting apparatus. For example, the laser cutting process may utilize a fiber laser.

Utilizing processes like laser cutting may be desirable for a number of reasons. For example, laser cutting processes may allow the shaft 12 to be cut into a number of different cutting patterns in a precisely controlled manner. This may include variations in the slot 18 width, ring width, beam height and/or width, etc. Furthermore, changes to the cutting pattern can be made without the need to replace the cutting instrument (e.g., blade). This may also allow smaller tubes (e.g., having a smaller outer diameter) to be used to form the shaft 12 without being limited by a minimum cutting blade size. Consequently, the shaft 12 may be fabricated for use in neurological devices or other devices where a relatively small size may be desired.

While not explicitly shown in the drawings, it can be appreciated that the optical fibers generally include a central core or mode field and outer jacket or cladding. For the purposes of this disclosure, the various optical fibers shown in the drawings may be understood to represent either the complete optical fiber (e.g., including the central core, outer cladding, and any other structure of the fiber) or just the central core or mode field of the fiber. As alluded above, the "outer diameter" of various optical fibers disclosed herein may be understood to represent either the outer diameter of the complete optical fiber (e.g., including the central core, outer cladding, and any other structure of the fiber) or just the outer diameter of central core or mode field of the fiber (e.g., the "mode field diameter", MFD).

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device system, comprising:
    a guidewire having a proximal end, the guidewire including a tubular member having a proximal region having a first wall thickness and a sensor region having a second wall thickness;
    wherein the second wall thickness is thinner than the first wall thickness;
    wherein the proximal region has a proximal outer diameter;
    wherein the sensor region has a sensor region outer diameter;
    wherein the proximal outer diameter is substantially equal to the sensor region outer diameter;
    wherein the tubular member defines an inner lumen
    wherein the inner lumen has a first diameter along the proximal region;
    wherein the inner lumen has a second diameter larger than the first diameter along the sensor region;
    an optical pressure sensor disposed within the inner lumen along the sensor region;
    a connector cable coupled to the proximal end of the guidewire, the connector cable having a proximal end;
    a signal conditioning unit coupled to the proximal end of the connector cable; and
    wherein one or more of the guidewire, the connector cable, and the signal conditioning unit includes an optical fiber having a core with a tapered outer diameter.

2. The system of claim 1, wherein the optical fiber having the core with the tapered outer diameter is disposed within the connector cable.

3. The system of claim 1, wherein the optical fiber having the core with the tapered outer diameter is disposed within the signal conditioning unit.

4. The system of claim 1, wherein the guidewire includes a second optical fiber that is coupled to the optical pressure sensor.

5. The system of claim 4, wherein the optical fiber having the core with the tapered outer diameter is disposed within the connector cable and wherein the second optical fiber is coupled to the optical fiber having the core with the tapered outer diameter.

6. The system of claim 5, wherein the optical fiber having the core with the tapered outer diameter is capable of receiving substantially all of a signal passing through the second optical fiber.

7. The system of claim 4, wherein the optical fiber having the core with the tapered outer diameter is disposed within the signal conditioning unit, wherein the second optical fiber is coupled to a third optical fiber disposed within the connector cable, and wherein the third optical fiber is coupled to the optical fiber with the tapered core.

8. The system of claim 7, wherein the optical fiber having the core with the tapered outer diameter is capable of receiving substantially all of a signal passing through the third optical fiber.

9. The system of claim 1, wherein the connector cable includes a distal connector and wherein the connector cable is coupled to the proximal end of the guidewire at the distal connector.

10. The system of claim 1, wherein the connector cable includes a proximal connector and wherein the signal conditioning unit is coupled to the proximal connector.

11. The system of claim 1, wherein the tubular member has a plurality of slots formed therein.

12. The system of claim 1, wherein the sensor region has an increased inner diameter.

13. A medical device system, comprising:
    a guidewire including a tubular member having radially continuous tube wall, the guidewire comprising a proximal region where the tube wall has a first wall thickness and a sensor housing region where the tube wall has a second wall thickness;

wherein the proximal region of the tubular member has an outer diameter that is constant with an outer diameter of the sensor housing region;

an optical pressure sensor disposed within the sensor housing region, the optical pressure sensor having a first optical fiber extending therefrom;

a connector cable capable of being coupled to a proximal end of the guidewire, the connector cable including a second optical fiber that is capable of being coupled to the first optical fiber;

a signal conditioning unit capable of being coupled to the connector cable, the signal conditioning unit including a third optical fiber that is capable of being coupled to the second optical fiber; and wherein at least one of the second optical fiber and the third optical fiber includes a core having at least a region with a tapered outer diameter.

14. The system of claim 13, wherein the second optical fiber has the core having the region with the tapered outer diameter.

15. The system of claim 14, wherein the second optical fiber is capable of receiving substantially all of a signal passing through the first optical fiber.

16. The system of claim 13, wherein the third optical fiber has the core having the region with the tapered outer diameter.

17. The system of claim 16, wherein the third optical fiber is capable of receiving substantially all of a signal passing through the second optical fiber.

18. A medical device system for determining fractional flow reserve, the system comprising:

a guidewire including a tubular member having a proximal region having a first wall thickness and a sensor housing region having a second wall thickness, the sensor housing region being disposed distally of the proximal region;

wherein the second wall thickness is thinner than the first wall thickness;

wherein the proximal region has a proximal outer diameter;

wherein the sensor housing region has a sensor housing outer diameter;

wherein the proximal outer diameter is substantially equal to the sensor housing outer diameter;

an optical pressure sensor disposed within the sensor housing region, the optical pressure sensor having a first optical fiber extending therefrom;

a connector cable capable of being coupled to a proximal end of the guidewire, the connector cable including a second optical fiber that is capable of being coupled to the first optical fiber;

wherein the second optical fiber includes a core having at least a region with a tapered outer diameter; and a signal conditioning unit capable of being coupled to the connector cable, the signal conditioning unit including a third optical fiber that is capable of being coupled to the second optical fiber.

19. The medical device of claim 18, wherein the second optical fiber is capable of receiving substantially all of a signal passing through the first optical fiber.

* * * * *